May 11, 1976 C. L. COOPER Plant Pat. 3,882
APPLE TREE - STARKSPUR
PRIME RED
Filed Dec. 24, 1974
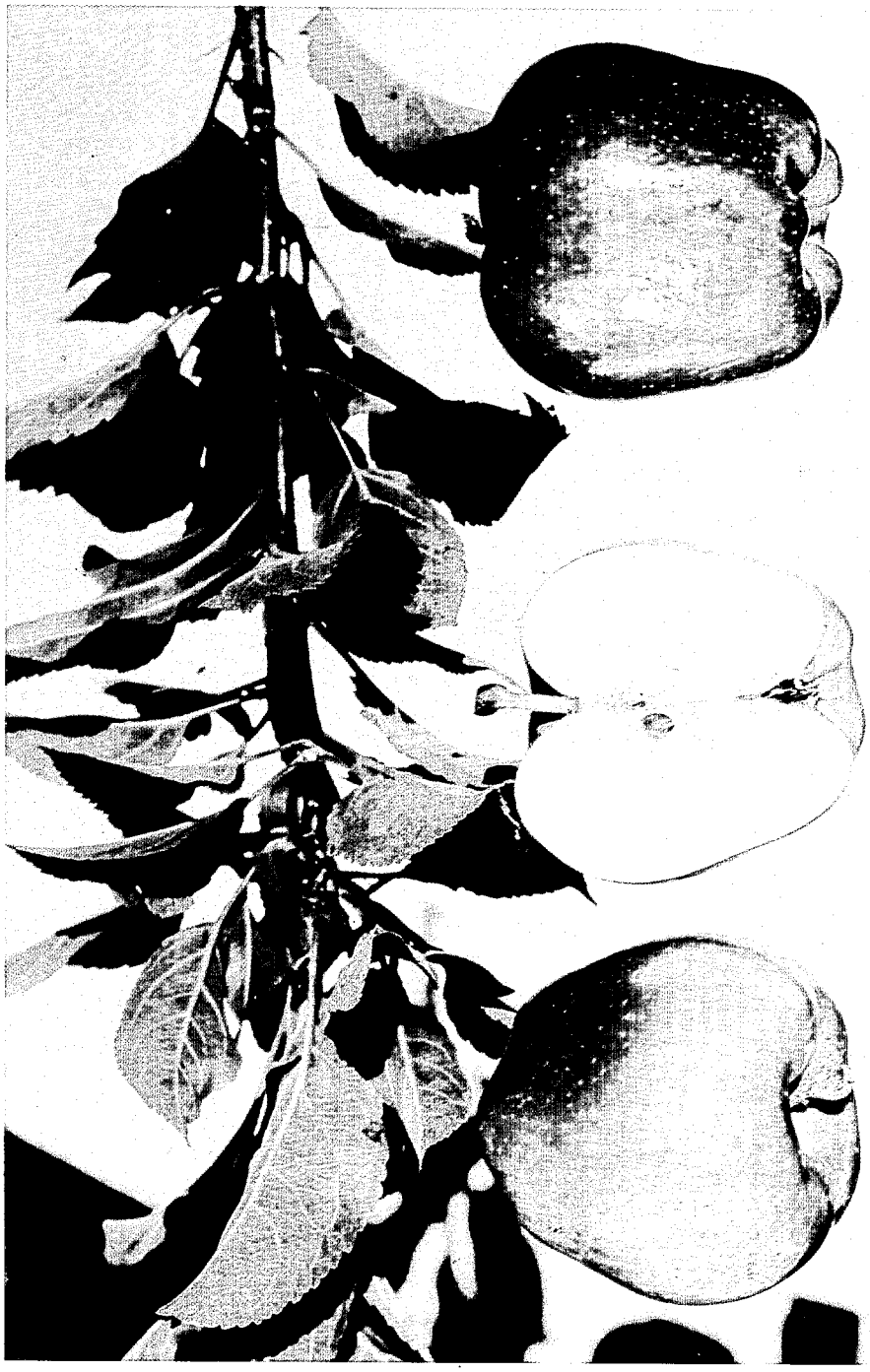

United States Patent

Plant Pat. 3,882

Patented May 11, 1976

3,882

APPLE TREE-STARKSPUR PRIME RED

Calvin L. Cooper, Brewster, Wash., assignor to Stark Brothers Nurseries & Orchards Co., Louisiana, Mo.

Filed Dec. 24, 1974, Ser. No. 536,198

Int. Cl. A01h *5/03*

U.S. Cl. Plt.—35 1 Claim

ABSTRACT OF THE DISCLOSURE

An apple tree of the Red Delicious type, originated as a bud mutation which was caused by irradiating twigs of Topred Delicious (P.P. No. 1,916).

SUMMARY OF THE INVENTION

This invention relates to improvements in apple trees of the Red Delicious type.

It was originated by me in Brewster, Wash., through irradiating twigs of Tropred Delicious (P.P. No. 1,916) with X-rays.

DETAILED DESCRIPTION OF DRAWING

The accompanying drawing shows typical specimens of the foliage and fruit of the new variety as depicted in color as nearly true as is reasonably possible to make the same in a color illustration of this character.

DETAILED DESCRIPTION OF DISCLOSURE

The following is a detailed description of my new variety with color terminology in accordance with Ridgway Color Standards and Nomenclature and with the Horticultural Color Guide, as indicated, except where general color terms of ordinary dictionary significance are obvious.

The specimens described were grown at Brewster, Wash.

The first and last picking was from about Sept. 20th through about Oct· 1st.

Tree: Medium small; upright, dense; vase-formed; medium slow growing; hardy; very productive; regular bearing.

Trunk: Stocky; smooth.

Branches: Thick; medium; smooth; little branching; Diamine brown (Plate XIII, Color No. 3′, tone M. Ridgway Color Standards). Lenticels: Medium few; medium small.

Leaves: Length, 2¼″ to 3⅛″; width 1⅝″; medium small; medium wide; medium short; ovate; taper-pointed; thick; Ivy Green (page 200, vol. 2, Color No. 0001060, Horticultural Color Guide); rugose.

*Margin.*—Coarsely serrate.

*Petiole.*—Length ⅝″ to ¾″; medium short; medium thick.

Fruit: Maturity when described eating: hard; ripe; Sept. 25, 1974.

*Size.*—Rather uniform; axial diameter 3″ to 3¼″; transverse 3″ to 3¼″; truncate at base ovoid; ribbed.

*Cavity.*—Symmetrical; abrupt; flaring toward apex, undulate; pubescent toward apex. Depth: ⅝″; breadth 1½″.

*Basin.*—Depth ⅝″; breadth 1¼″; markings Dull Green Yellow (Plate XVII Color No. 27′, Ridgway Color Standards).

Stem: Clubbed; stout; pubescent.

*Length.*—1″

*Breadth.*—⅛″

*Markings.*—Eugenia Red (Plate XIII, Color No. 1′, Ridgway Color Standards).

Calyx: Closed; persistent; broadly lanceolate; acute.

*Length.*—7/32″; approximate at base; reflexed from base at apex; coverged from base toward center; connivent.

*Outer surface.*—Pubescent.

*Inner surface.*—Pubescent.

Skin: Thick; tough; smooth; waxed.

*Dots obscure.*—Many; small; even; circular. Color of dots: white. Distribution of dots: most numerous toward basin.

*Ground color.*—Begonia Rose (Plate I, Color No· 1, tone B Ridgway Color Standards).

*Color markings.*—Striped; self-colored; bright.

*Color of markings.*—Carmine (Plate I, Color No. 1, tone i, Ridgway Color Standards).

*Bloom.*—Scant

*Scarfskin.*—Wanting

*General color effect.*—Bright red nearly covered with deeper red stripes.

Flesh: Juicy; satiny; white with greenish tint.

*Texture.*—Firm; fine; crisp.

*Flavor.*—Mild.

*Aroma.*—Distinct.

*Quality.*—Best.

Core: Median.

*Bundle area.*—Medium small; broadly ovate. Symmetrical.

*Halves of area.*—Equal.

*Bundles.*—Green tinge; inconspicuous; one whorl.

*Corelines.*—Meeting; in cross section indistinct; carpellary area indistinct; small.

*Calyx-tube.*—Glabrous toward base; funnel form.

*Stem of funnel.*—Short. Entire depth ⅛″.

*Styles present.*—Fleshy at base; united toward base; pubescent throughout.

*Stamens.*—One distinct whorl; median.

*Auxillary cavity.*—Present.

*Seed cells.*—Abaxial closed.

*Cell walls.*—Approximately thick; tough.

*Length.*—9/16″.

*Breadth.*—¼″. Longitudinal section ovate; acute at apex.

*Surface.*—Entire.

*Cross section.*—Narrow.

Seeds:

*Number perfect.*—2 to 3; imperfect 4 to 5.

*Number in one cell.*—1; length 5/16″.

*Breadth.*—7/32″.

*Form.*—Obtuse.

*Color.*—Walnut Brown (Plate XXVIII, Color No. 9″, tone k Ridgway Color Standards).

GENERAL NOTES

A detailed comparison, or contrast, of this variety of tree and fruit characters with some well known variety which it more or less closely resembles, reveals that the fruit of this apple tree is essentially identical with that of Topred Delicious (P.P. No. 1,916). The tree of Prime- Red is much smaller than Topred Delicious, with many more fruit spurs. PrimeRed is a typical "spur type" semi-dwarf, while Topred Delicious is a standard type tree. The tree is more compact than Starkrimson (P.P. No. 1,565).

I claim:

1. A new and distinct variety of apple tree, substantially as herein shown and described, characterized particularly as to novelty, by its similarity of fruit to Topred Delicious (P.P. No. 1,916), but distinguished therefrom by its much smaller growth and more compact form, and with many more fruit spurs.

No references cited.

ROBERT E. BAGWILL, Primary Examiner